United States Patent [19]
Uckun

[11] Patent Number: 5,919,457
[45] Date of Patent: *Jul. 6, 1999

[54] TXU-5/B53-PAP ANTIVIRAL BIOTHERAPEUTIC AGENT FOR THE TREATMENT OF AIDS

[75] Inventor: Fatih M. Uckun, White Bear Lake, Minn.

[73] Assignee: Regents of the University of Minnesota, Minneapolis, Minn.

[*] Notice: This patent issued on a continued prosecution application filed under 37 CFR 1.53(d), and is subject to the twenty year patent term provisions of 35 U.S.C. 154(a)(2).

[21] Appl. No.: 08/584,966

[22] Filed: Jan. 11, 1996

[51] Int. Cl.$^6$ ..................... A61K 39/395; A61K 39/40; A61K 39/42; A61K 39/44

[52] U.S. Cl. ..................... 424/183.1; 424/160.1; 435/70.21; 435/172.2; 435/339.1; 530/370; 530/379; 530/388.35; 530/389.4; 530/391.9

[58] Field of Search ................ 424/183.1, 160.1; 530/379, 370, 388.35, 389.4, 391.9; 435/70.21, 172.2, 339.1

[56] References Cited

FOREIGN PATENT DOCUMENTS

| | | |
|---|---|---|
| 0381763 | 8/1990 | European Pat. Off. . |
| WO91/01145 | 2/1991 | WIPO . |
| WO96/38751 | 12/1996 | WIPO . |

OTHER PUBLICATIONS

Piatier–Tonneau, D., et al., "Characterization of 18 Worshop anti–CD4 mAb: epitope mapping to CD4 mutants and effects on CD4–HLA class II interaction", *Leukocyte Typing*, 476–479, (1995).
Torbett, B.E., et al., "hu–PBL–SCID Mice: A Model for Human Immune Function, AIDS, and Lymphomagenesis", *Immunological Reviews*, 1991, No. 124, 139–164, (1991).
Mosier, D.E., et al., "Human Immunodeficiency Virus Infection of Human–PBL–SCID Mice", *Science*, vol. 251, 791–794, (Feb. 15, 1991).
McCune, J.M., et al., "Suppression of HIV Infection in AZT–Treated SCID–hu Mice", *Science*, vol. 247, 564–566, (Feb. 2, 1990).
Stirpe, F., et al., "Ribosome–inactivating proteins up to date", *FEBS Letters*, vol. 195, No. 1,2, 1–8, (Jan. 20, 1986).
Stirpe, F., et al., "Ribosome–inactivating Proteins from Plants: Present status and future prospects", *Bio/Technology*, vol. 10, 405–412, (Apr., 1992).
Dore, J.M., et al., "Mutations dissociating the inhibitory activity of the pokeweed antiviral protein on Eukaryote translation and *Escherichia coli* growth", *Nucleic Acids Research*, vol. 21, No. 18, 4200–4205, (Sep. 11, 1993).
Irvin, J.D., "Pokeweed antiviral protein", *Pharmacology & Therapeutics*, vol. 21, No. 3, 371–387, (1983).
Lord, M.J., et al., "Ribosome inactivating proteins of plants", *Cell Biology*, vol. 2, 15–22, (1991).
Haynes: Scientific and Social Issues of . . . : Science: vol. 260: pp. 1279–1286, 1993.
Haynes, et al.: Update on the issues of HIV. . . : the Finnish Medical Society DUODECIM, Ann Med: 28: pp. 39–41, 1996.
Dahlgleish, et al., *Nature*, 312, 763, (1984).
Erice, et al., *Clinical Infectious Diseases*, 18, 149, (1994).
Fauci, *Clin. Res.*, 32, 491, (1985).
Fauci, *Science*, 239, 617, (1988).
Fischl, et al., *Ann. Intern. Med.*, 112, 727, (1990).
Fischl, et al., *New Engl. J. Med.*, 317, 185, (1987).
Ho, et al., *New Engl. J. Med.*, 317, 278, (1987).
Lasky, et al., *Science*, 233, 209, (1986).
St. Clair, et al., *Science*, 253, 1557, (1991).
Venkatesan, *Science*, 241, 1481–1485, (1988).
Volberding, et al., *N. Engl. J. Med.*, 322, 941, (1990).
Yarchoan, et al., *Blood*, 78, 859, (1991).
Myers, D.E., et al., "Production of a pokeweed antiviral protein (PAP)–containing imjunotoxin, B43–PAP, directed against the CD19 human B lineage lymphoid differentiation antigen in highly purified form fo human clinical tials", *Jounal of Immunological Methods*, 136, pp. 221–238, (199).
Uckun, F.M., et al., "Effective Immunochemotherapy of CALLA+Cu+ Human Pre–B Acute lymphoblastic leukemia in mince with severe combined immunodeficiency using B43 (anti–CD19) pokeweed antiviral protein immunotoxin plus cyclophosphamide", *Blood*, vol. 79, No. 12, pp. 3116–3129, (Jun. 15, 1992).
Fox: No winners againt AIDS: Bio/Tech: vol. 12: p. 128, Feb. 1994.
Cohen: Jitters jeopardize AIDS vaccine trails: Science: vol. 12: pp. 980–981, Nov. 1993.
Zarling, et al. : Inhibition of HIV replication . . . : Nature:. vol. 347: pp. 92–95, Sep. 1990.
Piatier–Tonneau, et al. : Characterisatic. of 18 workshop anti–CD4 mAb: . . . : Leukocyte Typ. V: pp. 476–479, 1995.
Irvin, et al. : Pokeweed antiviral protein . . . : Pharm. Ther.: vol. 55: pp. 279–302, 1992.
Zarling, et al. : Inhibition of HIV replication in seropositive patients . . . : Int. J. Immuno.: vol. 13, Suppl. 1: pp. 63–68, 1991. Duplicate.
Erice, et al. : Anti–human immundeficiency virus . . . :Anti mich. Ag. Chemother. : vol. 37, No. 4: pp. 835–838, 1993. Duplicate.

*Primary Examiner*—Frank C. Eisenschenk
*Assistant Examiner*—Brett Nelson
*Attorney, Agent, or Firm*—Schwegman, Lundberg Woessner & Kluth P.A.

[57] ABSTRACT

Immunoconjugates comprising the monoclonal antibody TXU-5/B53 linked to pokeweed antiviral protein or bioactive subunits thereof are provided which are effective for the treatment of mammalian HIV infection.

13 Claims, 9 Drawing Sheets

Spleen

FIG. 3B

Peritonal Lavage

Peritoneal Cavity Cells

FIG. 6A

FIG. 6B

| | NEG CON | POS CON | PBS | | | ZDV | | | α CD4-PAP | | | α CD4-PAP +ZDV | | |
|---|---|---|---|---|---|---|---|---|---|---|---|---|---|---|
| | | | 1 | 2 | 3 | 1 | 2 | 3 | 1 | 2 | 3 | 1 | 2 | 3 |
| HIV-1 PCR | − | + | + | + | + | + | + | + | − | − | − | − | − | − |
| HIV-1 Culture | − | NA | + | + | + | + | + | + | − | − | − | − | − | − |

5,919,457

TXU-5/B53-PAP ANTIVIRAL BIOTHERAPEUTIC AGENT FOR THE TREATMENT OF AIDS

BACKGROUND OF THE INVENTION

The acquired immunodeficiency syndrome (AIDS) and infection with the human immunodeficiency virus type 1 (HIV-1) constitute a worldwide public health problem. Venkatesan, *Science*, 241, 1481–1485 (1988). HIV is an RNA retrovirus that was originally designated human T-lymphotropic virus (HTLV-III), lymphadenopathy-associated virus (LAV), or AIDS associated retrovirus (ARV). Fauci, *Science*, 239, 617 (1988). HIV is commonly referred to as HIV-1 to differentiate it from HIV-2, a clinical syndrome indistinguishable from HIV-induced AIDS which has been isolated from West African patients. The virus shares many features with other members of the nontransforming and cytopathic lentivirus family of retroviruses.

The critical basis for the immunopathogenesis of HIV infection is the depletion of the CD4+ helper/inducer subset of T-cells, resulting in profound immunosuppression. See Dahlgleish et al, *Nature*, 312, 763 (1984); Fauci, *Clin. Res.*, 32, 491 (1985), Ho et al. *N. Engl. J. Med.*, 317, 278 (1987). HIV has a selective tropism for $CD4^+$ T-cells and macrophages which is mediated by interaction of its envelope (env) protein gp120 with an essential component of the cell surface receptor for HIV-1, the CD4 antigen. Lasky et al. *Science*, 233, 209 (1986). After HIV binds to the first domain of the CD4 molecule via the external envelope glycoprotein gp 120, the virus is internalized and uncoated. Fauci, *Science*, 239, 617 (1988). Once uncoated, the viral genomic RNA is transcribed to DNA by the enzyme reverse transcriptase. The proviral DNA is then integrated into the host chromosomal DNA. After integration of the provirus, the infection may assume a latent phase or the proviral DNA may transcribe viral genomic RNA and messenger RNA. Protein synthesis, processing, and virus assembly occur with budding of the mature virion from the cell surface.

At present, AIDS is incurable and treatment modalities that reduce HIV-1 replication in vivo by using reverse transcriptase inhibitors such as zidovudine/ZDV (formerly termed azidothymidine/AZT) and dideoxyinosine (ddI) cause substantial side effects. Yarchoan et al., *Blood*, 78, 859 (1991). Although ZDV delays the disease progression in HIV-1 seropositive asymptomatic individuals and has improved the survival of patients with AIDS and AIDS-related complex (ARC), the therapeutic response is frequently transient. Volberding et al., *N Engl J Med*, 322, 941 (1990); Fischl et al., *Ann Intern Med*, 112, 727 (1990); Fischl et al., *N Engl J Med*, 317, 185 (1987). Variants of HIV-1 that are resistant to ZDV emerge to thwart the success of continued therapy. Erice et al., *Clinical Infectious Diseases*, 18, 149 (1994). Recent data indicate that resistance among HIV-1 isolates also emerges during dideoxyinosine (ddI) therapy. St Clair et al., *Science*, 253, 1557 (1991). These characteristics emphasize the resilience of HIV-1 and the need for more powerful strategies against this virus.

It has been reported that HIV-1 replication in normal $CD4^+$ T cells can be inhibited in vitro by pokeweed antiviral protein (PAP). Zarling et al., *Nature* 347: 92–95, (1990). Notably, targeting PAP to CD4+ T cells in vitro by conjugating it with monoclonal antibodies reactive with $CD4^+$ T-cells increased its potency >1,000-fold in inhibition of HIV-1 replication (Zarling et al., *Nature* 347: 92–95, 1990; U.S. patent application Ser. No. 07/979,470). Subsequent studies using clinical isolates of AZT-sensitive and AZT-resistant HIV-1 demonstrated that G17.2(anti-CD4)-PAP immunoconjugate exhibits potent anti-HIV activity against all isolates at nanomolar concentrations (Erice et al., *Antimicrobial Agents and Chemotherapy* 37: 835–838, 1993). Despite these very encouraging in vitro data, the clinical development of PAP immunoconjugates for treatment of HIV-1 infected individuals has been hampered by the poor in vivo stability of anti-T cell directed immunoconjugates. Consequently, therapeutic concentrations of T-cell directed PAP immunoconjugates were impossible to attain in vivo. For example, G17.2(anti-CD4)-PAP immunoconjugate (disclosed in U.S. patent application Ser. No. 07/979,470) showed no detectable anti-HIV-1 activity in SCID mouse models of human AIDS. Thus, a need exists for an anti-T cell PAP immunoconjugate with improved stability that is efficacious in vivo.

SUMMARY OF THE INVENTION

The present invention provides antiviral biotherapeutic agents comprising a monoclonal antibody specific to T-cells linked to an effective antiviral amount of pokeweed antiviral protein (PAP). These antiviral immunoconjugates are useful for the treatment of AIDS, ARC or HIV infection. Furthermore, the immunoconjugates of the present invention are active both in vitro and in vivo, and these are specifically asserted utilities for the present compound. Preferably, the immunoconjugate of the present invention employs the monoclonal antibody TXU-5/B53, which binds to the CD4 antigen present at the surface of virus-infected mammalian cells. More preferably, the antibody utilized in the practice of the present invention has the binding specificity of the monoclonal antibody produced by hybrid cell line ATCC designation HB-12261. As described herein, the term "immunoconjugate" refers in general to a monoclonal antibody (MoAb) and antiviral protein conjugate wherein the antibody is covalently bonded or cross-linked to the antiviral protein. More specifically, the immunoconjugate of the present invention includes the monoclonal antibody TXU-5/B53, which reacts with the HIV-1 binding site of the surface CD4 receptor on human cells. TXU-5/B53 is covalently linked to pokeweed antiviral protein (PAP) or any biological equivalent from whatever source derived, including subunits and derivatives thereof. As used herein, the term "PAP" refers to any antiviral pokeweed antiviral protein, or subunit, variant or mutant thereof, including subtypes PAP-II, PAP-S, and recombinant PAP. The term "antiviral amount" is defined to mean an amount of PAP that inhibits HIV-1 replication in human cells once the immunoconjugate has associated with the $CD4^+$ human cells.

The present invention also provides a method for inactivating or inhibiting replication of HIV in mammalian cells which comprises treating a patient afflicted with an HIV infection, ARC or AIDS with the immunoconjugate of the present invention. The present method is especially suited for the treatment of patients infected with HIV strains that have become ZDV resistant.

Functional impairment and selective depletion of $CD4^+$ cells results at least in part because HIV-1 binds to the CD4 molecule and infects $CD4^+$ cells. The immunoconjugate of the present invention exerts its effect by targeting a potent antiviral agent to virus-infected $CD4^+$ cells. However, in some cases, combined or adjunctive therapies may be necessary to assist in the elimination of any PAP-resistant mutants should they exist or emerge. In this regard, Applicant has discovered that the immunoconjugate of the present invention can be utilized in combination with nucleoside analogs such as the reverse transcriptase inhibitor zidovudine (formerly AZT), without losing its antiviral activity or causing undesirable side effects. Therefore, one embodiment of the present invention comprises the administration of TXU-5/B53-PAP in combination with an effective amount of one or more conventional anti-AIDS agents. Preferably, the agent employed is a reverse transcriptase inhibitor. Most preferably, the agent employed is ZDV.

Unlike immunoconjugates that rely on the expression of HIV-1 envelope proteins on infected cells to provide them with binding targets, the immunoconjugate of the present invention targets pokeweed antiviral protein (PAP) to uninfected or latently infected CD4+ cells using monoclonal antibodies against normal antigens on CD4+ cells. Applicants have discovered that this approach avoids potential problems caused by envelope antigen heterogeneity among different HIV-1 isolates or the presence of host anti-envelope antibodies. It had been previously discovered by Applicant, and described in U.S. patent application Ser. No. 07/979,470, which application is incorporated herein by reference, that the internalization of PAP-monoclonal antibody conjugates by MoAb receptor-mediated endocytosis results in increased delivery of PAP through the plasma membrane, as compared to the non-specific uptake that occurs at high PAP concentrations.

However, the PAP immunoconjugates disclosed in the '470 application displayed very poor in vivo stability and showed no anti-HIV activity in SCID mouse models of human AIDS. Applicant has now discovered the immunoconjugate of the present invention, which exhibits surprising in vivo stability as measured by longer serum half-life and greater systemic exposure. For example, a 1 mg dose of G17-2(anti-CD4)-PAP, disclosed in U.S. patent application Ser. No. 07/979,470, generated a systemic intact immunoconjugate exposure level of 3.8 μg×hour/L in 4 kg rabbits. In contrast, the immunoconjugate of the present invention (TXU-5/B53(anti-CD4)-PAP) administered at the same dose of 1 mg/rabbit generated a systemic intact immunoconjugate exposure level of 67.5 μg×hour/L, a 17.8-fold increase over the immunoconjugate disclosed in '470. As a result, therapeutic concentrations of the present immunoconjugate, TXU-5/B53-PAP, can be achieved in vivo. Most importantly, TXU-5/B53-PAP showed potent anti-HIV-1 activity in a SCID mouse model of human AIDS without causing systemic toxicity. Furthermore, Applicant made the surprising discovery that the immunoconjugate of the present invention can be concurrently administered with AZT (ZDV) without causing undesired side effects.

It is expected that the immunoconjugate of the present invention will provide the basis for a highly effective procedure to inhibit HIV replication in mammalian monocytes and T-cells; thereby providing a method to treat patients with AIDS, ARC or asymptomatic patients infected with HIV-1 who have not yet developed AIDS. It is further expected that the present immunoconjugate will provide the basis for an effective method to inhibit other retroviruses (HTLV-1, etc.) and viruses other than retroviruses such as, but not limited to, members of the herpes virus group (HSV, CMV, EBV), influenza viruses, rhinoviruses, papovaviruses (human papilloma), adenoviruses, hepatitis virus, and the like. Finally, it is expected that the immunoconjugate of the present invention will be effective in the treatment of diseases or pathologies associated with undesirable T-cell proliferation, either alone or in combination with conventional therapies for such afflictions. Such pathologies include cancers, such as T-cell leukemias or lymphomas, organ rejection, rejection of bone marrow transplants or autoimmune diseases such as systemic lupus erythematosus, rheumatoid arthritis, non-glomerular nephrosis, psoriasis, chronic active hepatitis, ulcerative colitis, Crohn's disease, Behqet's disease, chronic glomerulonephritis (membranous), chronic thrombocytopenic purpura, and autoimmune hemolytic anemia.

BRIEF DESCRIPTION OF THE DRAWINGS

FIGS. 1A and 1B depict the in vitro activity of TXU-5/B53-PAP against two AZT resistant HIV-1 isolates.

FIGS. 2A and 2B depict the in vivo stability of a comparison of the in vivo stability of G17.2(anti-CD4)-PAP versus TXU-5/B53-PAP.

FIGS. 3A and 3B illustrate the presence of xenografted human lymphocytes in the spleen and peritoneal lavage specimens from both uninfected and HIV infected SCID mice.

FIGS. 4A, 4B, 4C, 4D, 4E, and 4F depict the results of multi-parameter flow cytometric analysis of coexpression of CD4 and gpl120 antigens on the surface of lymphocytes obtained from the peritoneal cavities of ZDV-treated or TXU-5/B53-PAP treated mice.

FIGS. 5A and 5B depict the HIV-1 PCR and culture results from the spleen cells of Hu-PBL-SCID mice challenged with HIV-1 and treated with PBS, ZDV, TXU-5/B53-PAP or a combination of TXU-5/B53-PAP plus ZDV.

FIGS. 6A and 6B depict the HIV-1 PCR and culture results from the periotoneal cavity cells of Hu-PBL-SCID mice challenged with HIV-1 and treated with PBS, ZDV, TXU-5/B53-PAP or a combination of TXU-5/B53-PAP plus ZDV.

DETAILED DESCRIPTION OF THE INVENTION

The present invention is directed to an immunoconjugate useful in the treatment of mammalian viruses, including retroviruses such as HTLV-1, HTLV-11, SIV, HIV-1 and HIV-2 or the like. Specifically, the present invention provides an immunoconjugate useful in the treatment of ARC, AIDS, or asymptomatic infection.

A. Monoclonal Antibodies

Monoclonal antibodies (MoAbs) are produced by the fusion of spleen lymphocytes with malignant cells (myelomas) of bone marrow primary tumors. Milstein, *Sci. Am.*, 243, 66 (1980). The procedure yields a hybrid cell line, or hybridoma, arising from a single fused cell hybrid, or clone, which possesses characteristics of both the lymphocytes and myeloma cell lines. Like the lymphocytes (taken from animals primed with sheep red blood cells as antigens), the fused hybrids or hybridomas secrete antibodies (immunoglobulins) reactive with the antigen. Moreover, like the myeloma cell lines, the hybrid cell lines are immortal. Specifically, whereas antisera derived from vaccinated animals are variable mixtures of antibodies which cannot be identically reproduced, the single-type of immunoglobulin secreted by a hybridoma is specific to one and only one determinant on the antigen, a complex molecule having a multiplicity of antigenic molecular substructures, or determinants (epitopes). Hence, monoclonal antibodies raised against a single antigen may be distinct from each other depending on the determinant that induced their formation. However, all of the antibodies produced by a given clone are identical. Furthermore, hybridoma cell lines can be reproduced indefinitely, are easily propagated in vitro and in vivo, and can yield monoclonal antibodies in extremely high concentrations.

Monoclonal antibodies have largely been applied clinically to the diagnosis and therapy of cancer, the modulation of the immune response to produce immunosuppression for treatment of autoimmune and graft versus host diseases (GVHD) and for prevention of allograft rejection. Human monoclonal antibodies have also been applied clinically against cytomegalovirus, *Varicella zoster* virus, and the various specific serotypes of *Pseudomonas aeruginosa, Escherichia coli,* and *Klebsiella pneumoniae.*

Monoclonal antibodies useful in the present invention are produced using well known hybridoma fusion techniques [G. Kohler and C. Milstein, *Eur. J. Immunol.,* 6: 511 (1976); M. Shulman et al., *Nature,* 276: 269 (1978)]. As indicated above, the present invention uses a monoclonal antibody directed against T-cells. Preferably, the specific antibody employed is TXU-5/B53.

1. TXU-5/B53 Monoclonal Antibody.

TXU-5/B53 is a murine IgG1 monoclonal antibody directed against CD4 antigen. CD4 antigen, which is expressed on human T cells as well as monocytes, is the receptor for the envelope protein gpl120 of HIV-1. The gpl120 binding site of CD4 has been well characterized and mapped to a region encompassing residues 39–59 within the first domain (D1) of CD4. The binding site of TXU-5/B53 on CD4 receptor has been determined to be the first domain (epitope: CDR2, C'C"D strands) of CD4 during the Fifth International Workshop on Human Leukocyte Differentiation Antigens (Piatier-Tonneau et al., [In] Leukocyte Typing V, Oxford University Press, 1995; pp 476–479). Specifically, binding of TXU-5/B53 antibody to CD4 positive COS cells was lost when the COS cells were transfected with a deletion mutant of CD4 lacking amino acid residues 43–49 within the first domain. Furthermore, TXU-5/B53 antibody inhibited radioiodinated HIV envelope protein gpl120 binding to CD4 positive cells by 100% (Piatier-Tonneau et al., [In] Leukocyte Typing V, Oxford University Press, 1995; pp 476–479).

B. Pokeweed Antiviral Protein (PAP).

Pokeweed antiviral protein (PAP) is an antiviral agent isolated from the leaves or seeds of Phytolacca americana (Irvin and Uckun, *Pharmacology and Therapeutics* 55: 279, 1992). PAP displays broad-spectrum antiviral activity against plant viruses, herpes simplex virus, cytomegalovirus, poliovirus, and influenza virus. Aron et al., *Agents Chemotherapy,* 17, 1032 (1980). In fact, pokeweed antiviral protein was discovered due to its ability to inhibit the transmission of tobacco mosaic virus (TMV) in plants and it was subsequently demonstrated that the purified protein was equally effective against a number of other plant viruses. Tomlinson et al., *J. Gen. Virol.,* 22, 225 (1974).

The antiviral activity of PAP can be greatly enhanced and made highly cell selective by conjugation to antibodies specific for cell-surface receptors. One such immunoconjugate containing PAP has been developed by the Applicant and tested against another member of the herpes family, human cytomegalovirus (HCMV). In this study, the antiviral action of PAP was found to be enhanced by chemically coupling it to an antibody. Gehrz et al., "Treatment of human cytomegalovirus (HCMV) with novel antiviral immunoconjugates", in Progress in *Cytomegalovirus Research,* Landin, M. P. Ed., Elsevier Science Publishers BV, Amsterdam, p. 353 (1991). PAP-antibody conjugates were prepared with monoclonal antibodies specific for the low density lipoprotein receptor (LDLr) and the HCMV envelope glycoprotein gp55, which is expressed on HCMV infected cells, and tested for antiviral effects. The conjugate prepared with PAP and anti-LDLr increased the antiviral action of PAP 1000-fold, resulting in 50% reduction in plaque formation at 1 ng/ml,. Conjugation of PAP to anti-gp55 did not increase the antiviral activity observed for PAP alone. Gehrz et al., cited supra. These studies show that the antiviral activity of PAP can be significantly increased by conjugation to cell surface directed antibodies but that the antibodies must be targeted to cell surface proteins that are capable of being internalized.

Unconjugated PAP has been shown to have anti-HIV and abortifacient properties comparable to those reported for trichosanthin. Teltow et al., *Antimicrob. Ag. Chemother.,* 23, 390 (1983). It has been reported that PAP inhibits HIV-1 production of p24 in both T cells and macrophages infected in vitro with an $ID_{50}$ of approximately $5 \times 10^3$ pM after treating cells for 4 hours prior to infection. Zarling et al., *Nature,* 347, 92 (1990). These studies also demonstrated that uninfected cells were not adversely affected by PAP treatment at concentrations of up to 30 nM.

Notably, targeting PAP to CD4+ T cells in vitro by conjugating it with monoclonal antibodies reactive with $CD4^+$ T-cells increased its potency >1,000-fold in inhibition of HIV-1 replication (Zarling et al., *Nature* 347: 92–95, 1990; U.S. patent application Ser. No. 07/979,470). Subsequent studies using clinical isolates of AZT-sensitive and AZT-resistant HIV-1 demonstrated that G17.2(anti-CD4)-PAP immunoconjugate exhibits potent anti-HIV activity against all isolates at nanomolar concentrations (Erice et al., *Antimicrobial Agents and Chemotherapy* 37: 835–838, 1993). However, despite this very encouraging in vitro data, the clinical development of PAP immunoconjugates for treatment of HIV-1 infected individuals has been hampered by the poor in vivo stability of anti-T cell directed immunoconjugates. Consequently, therapeutic concentrations of T-cell directed PAP immunoconjugates in vivo were unachievable. For example, the G17.2(anti-CD4)-PAP immunoconjugate disclosed in U.S. patent application Ser. No. 07/979,470 showed no detectable anti-HIV-1 activity in SCID mouse models of human AIDS.

C. Production and Purification of TXU-5/B53-PAP Immunoconjugate

Preferred TXU-5/B53-PAP immunoconjugates of the present invention are formed by linking an effective antiviral amount of PAP molecules to each molecule of TXU-5/B53. For example, a reagent useful in the practice of the invention is an about 1:1 mixture of TXU-5/B53-PAP species having one and two PAP molecules per TXU-5/B53 molecule, respectively.

The particular TXU-5/B53-PAP immunoconjuugate employed in Examples 2–4 hereinbelow is prepared by linking TXU-5/B53 MoAb to PAP as described in U.S. Pat. No. 4,831,117, to Uckun, which is incorporated herein by reference. A hybridoma secreting TXU-5/B53 is available from the ATCC under designation HB12261. Further information concerning the production and purification of TXU-5/B53-PAP can be found in Example 1. However, TXU-5/B53 can be linked to effective amounts of PAP by other means disclosed in the art, including those taught in U.S. Pat. Nos. 4,363,758, Masuho et al.; 5,167,956, Neville, Jr. et al. and 4,340,535, Voisin et al. For example, in addition to N-succinimidyl 3-(2-pyridyldithio)propionate (SPDP), 4-succinimidyloxycarbonyl-methyl-(2-pyridyldithio)-toluene (SMPT) and N-succimidyl 6-[3-(2-pyridyldithio)propionamido]hexanoate (LC-SPDP) may be used as linking agents.

D. Modes of Administration of TXU-5/B53-PAP

The present immunoconjugate can be formulated as pharmaceutical compositions and administered to a human or other mammal afflicted with AIDS, alone or in combination in a unit dosage form comprising an effective amount of one or more of these agents in combination with a pharmaceutically acceptable carrier or vehicle.

1. Dosage Forms

It is preferred that the TXU-5/B53-PAP immunoconjugate of the present invention be parenterally administered, i.e., intravenously, intramuscularly, or subcutaneously by infusion or injection. Solutions or suspensions of the immunoconjugate can be prepared in water, or isotonic saline, such as PBS, optionally mixed with a nontoxic surfactant. Dispersions can also be prepared in glycerol, liquid polyethylene glycols, DMA, vegetable oils, triacetin, liposomes, and mixtures thereof. Under ordinary conditions of storage and use, these preparations may contain a preservative to prevent the growth of microorganisms.

The pharmaceutical dosage form suitable for injection or infusion use can include sterile aqueous solutions or dispersions or sterile powders comprising the immunoconjugate which are adapted for the extemporaneous preparation of sterile injectable or infusible solutions or dispersions. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, and liquid polyethylene glycols, and the like), vegetable oils, nontoxic glycerol esters, lipids (for example, dimyristoyl phosphatidyl choline) and suitable mixtures thereof. The proper fluidity can be maintained, for example, by the formation of liposomes, by the maintenance of the required particle size in the case of dispersion or by the use of nontoxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers or sodium chloride. Prolonged absorption of the injectable compositions can be brought about by the inclusion in the compositions of agents delaying absorption, for example, aluminum monostearate hydrogels and gelatin.

Sterile injectable or infusable solutions are prepared by incorporating the immunoconjugate in the required amount in the appropriate solvent with various of the other ingredients enumerated above, and as required, followed by filter sterilization. In the case of sterile powders for the preparation of sterile injectable or infusable solutions, the preferred methods of preparation are vacuum drying and the freeze drying techniques, which yield a powder of the active ingredient plus any additional desired ingredient present in the previously sterile-filtered solutions.

Furthermore, suitable formulations for the immunoconjugate of the present invention include those suitable for oral or rectal administration. The formulations may be prepared by any of the methods well known in the art of pharmacy. Such methods include the step of bringing into association the immunoconjugate with liquid carriers or finely divided solid carriers or both and then, if necessary, shaping the product into the desired formulation.

Pharmaceutical formulations suitable for oral administration may conveniently be presented as discrete units such as capsules, sachets, or tablets, each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, nonaqueous vehicles (which may include edible oils), or preservatives.

Additionally, the immunoconjugate of the present invention is well suited to formulation or controlled release dosage forms. The formulations can be so constituted that they release the active dry ingredient only or preferably in a particular physiological location, optionally over a period of time. The coatings, envelopes, and protective matrices may be made, for example, from polymeric substances or waxes. The compounds can also be delivered via patches for transdermal delivery, subcutaneous implants, infusion pumps or via release from implanted depot sustained release dosage forms.

2. Dosages

The dosage of the immunoconjugate in said composition can be varied widely, in accord with the size, age and condition of the patient and the target cancer. However, the dose should be sufficient to inhibit a substantial portion, usually more than about 90%, of the virus replication in infected cells of the patient. Specifically, TXU-5/B53-PAP would inhibit HIV-replication by >90% if used at 10–100 pM range, which is equal to 2.0–20 ng/ml. The dose required to achieve this concentration can be calculated using the formula: Dose in micrograms=70×2(20)×wt (in kg)/1,000. For a 70 kg patient, this would yield 10–100 micrograms. Dosages for adult humans with HIV infection envisioned by the present invention and considered to be therapeutically effective will therefore range from between about 10 and 100 micrograms and will be administered with a frequency based on the plasma half life of TXU-5/B53-PAP immunoconjugate in a given patient, as determined by solid phase ELISA. Higher doses can be employed in some cases, and the doses can readily be adjusted to provide appropriate amounts of the immunoconjugate to children using the above formula.

The invention will be further described by reference to the following detailed examples.

EXAMPLE 1

Preparation and Purification of TXU-5/B53-PAP Immunoconjugate

Affinity purified TXU-5/B53 (IgG1, αCD4) MoAb was conjugated to 2-iminothiolane-modified PAP from spring leaves of *Phytolacca americana* or PAP mutants using the heterobifunctional crosslinking agent N-succinimidyl 3-(2pyridyldithio) propionate (SPDP), according to previously described procedures (Uckun et al., *J. Exp. Medicine*, 163, 347 (1986)). TXU-5/B53-PAP immunoconjugate was then purified from unconjugated TXU-5/B53-MoAb and free PAP by size exclusion HPLC and cation exchange chromatography, as previously described in detail by Uckun et al. in *J. Exp. Medicine*, 163, 347 (1986). The purity, immunoreactivity, ribosome-inhibiting activity and composition of TXU-5/B53-PAP immunoconjugate was determined, as previously reported by Uckun et al., cited supra. Controls included unconjugated PAP, B43(αCD19)-PAP directed against B-cells, and unconjugated TXU-5/B53 antibody. The control reagents were prepared using procedures previously published by Uckun et al., cited supra.

SDS-PAGE (5% separating gel) was used to monitor the purity and composition of the TXU-5/B53-PAP. Uckun et al., cited supra. Gels were stained with Coomassie Blue G-250, destained in 10% acetic acid/30% methanol, dried, and subsequently scanned using a Beckman DU62 spectrophotometer and Gel Scan Soft-Pac Module (Beckman Instruments). In addition, a silver stain kit obtained from Bio-Rad Laboratories was utilized to visualize the protein bands after SDS-PAGE with greater sensitivity of detection. Uckun et al., cited supra. The presence of TXU-5/B53 and PAP moieties in the TXU-5/B53-PAP immunoconjugate was confirmed using Western blot analysis and a detection kit obtained from Bio-Rad Laboratories. Uckun et al., cited supra. The anti-PAP primary antibody was generated in rabbits which have been hyperimmunized with highly purified PAP. Immunoblotting was also done using alkaline phosphatase conjugated goat anti-mouse IgG (Sigma Chemical Co., St. Louis, Mo.) to detect unconjugated TXU-5/B53 remaining in the purified immunoconjugate preparations. Uckun et al., cited supra. Protein concentrations were determined using the Bicinchoninic Assay System obtained from Sigma Chemical Co. (St. Louis, Mo.). The ribosome-inhibiting activity of the PAP moiety in the TXU5/B53-PAP immunoconjugate was analyzed in an mRNA-dependent cell-free translation system obtained in kit form from Promega Biotech inc. (Madison, Wis.). Uckun et al., cited supra.

EXAMPLE 2

Figure 1A:
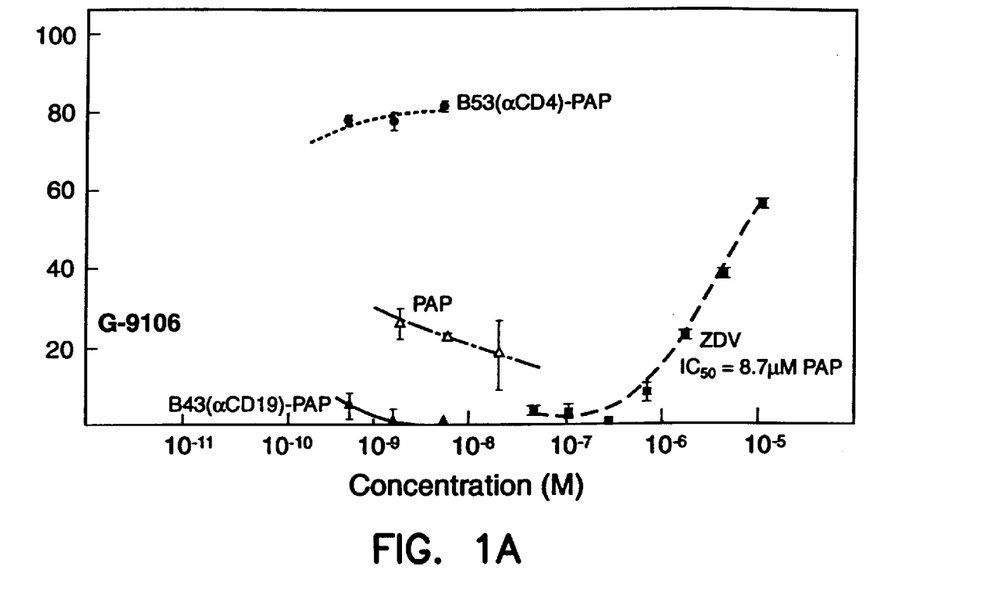
Figure 1B:
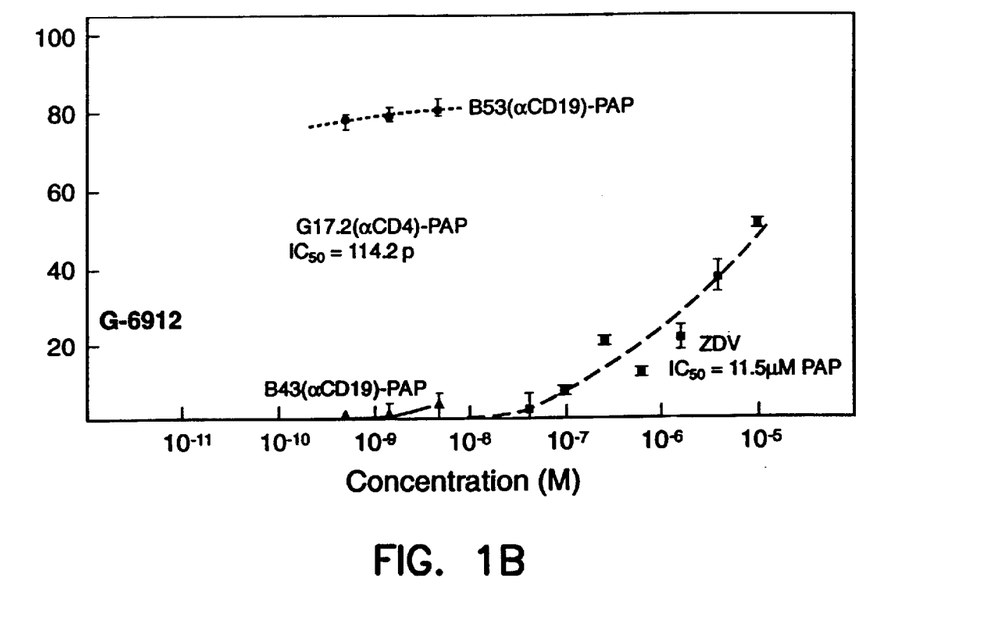

In Vitro Antiviral Activity of TXU-5/B53-PAP Immunoconjugate Against AZT-Resistant AIDS Virus The antiviral activity of TXU-5/B53-PAP was tested against two zidovudine (ZDV=AZT)-resistant HIV-1 isolates, namely G-9106 (ZDV $IC_{50}$ [the concentration at which 50% of the reverse transcriptase activity is inhibited] =8.7 $\mu$M), and G-6912 (ZDV $IC_{50}$=1.5 $\mu$M) (Larder et al., Science, 243, 1731 (1989)) using in vitro reverse transcriptase inhibition assays, as previously described by Erice et al. in Antimicrobial Agents and Chemotherapy, 37, 835 (1993). As illustrated in FIG. 1, TXU-5/B53-PAP inhibited replication of both isolates at nanomolar concentrations. Thus, TXU-5/B53-PAP is a >1,000-fold more potent antiviral agent than AZT against these AZT-resistant HIV-1 isolates. Unlike TXU-5/B53-PAP, the negative control PAP immunoconjugate B43(anti-CD19)-PAP, which does not react with T-cells, did not inhibit HIV-1 replication.

EXAMPLE 3

In Vivo Stability of TXU-5/B53-PAP Immunoconjugate

Figure 2A:
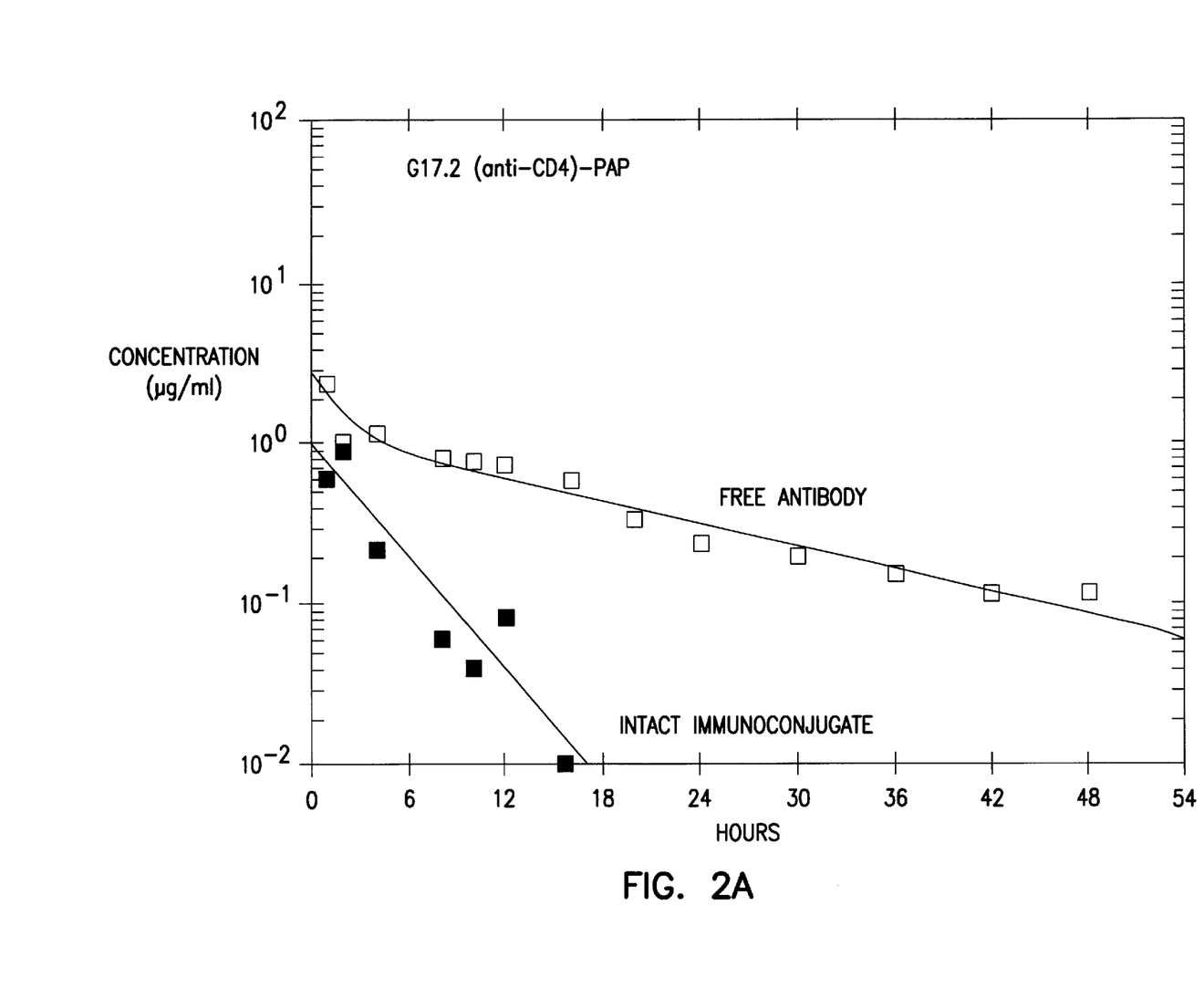
Figure 2B:
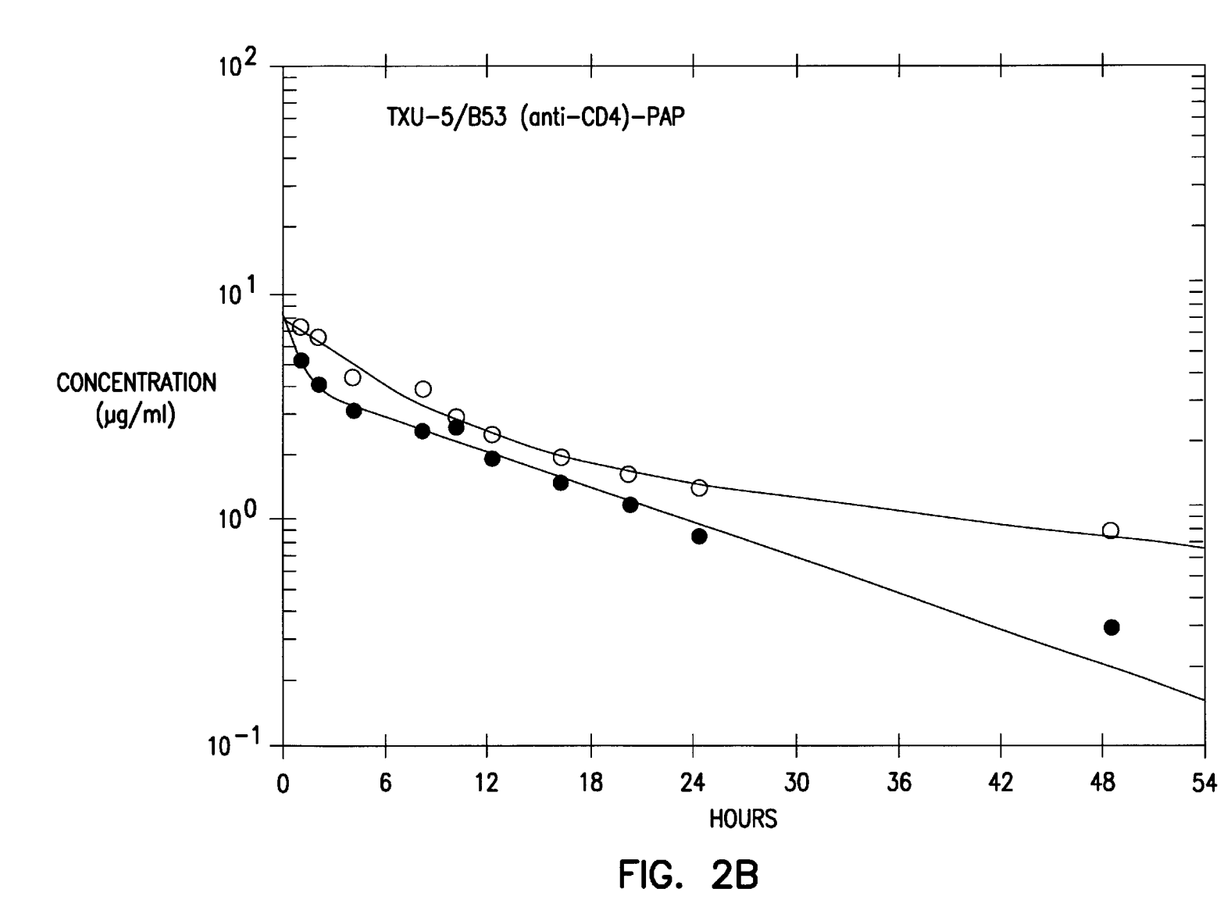

The PAP immunoconjugates disclosed in the U.S. patent application Ser. No. 07/979,470 displayed very poor in vivo stability and showed no anti-HIV activity in SCID mouse models of human AIDS. To compare the in vivo stability of TXU-5/B53(anti-CD4)-PAP immunoconjugate of the present invention with the in vivo stability of the G17.2 (anti-CD4)-PAP immunoconjugate disclosed in the '470 application, New Zealand white female rabbits weighing 3 kg were injected intravenously with a 1 mg dose of these agents. Peripheral blood was obtained by retroorbital venipuncture at multiple time points following the administration of the immunoconjugates and serum concentrations of intact immunoconjugate as well as unconjugated antibody were determined by solid phase ELISA, as previously described (Uckun et al., Leukemia and Lymphoma 9: 459–476, 1993; Myers et al., Leukemia and Lymphoma 18: 93–102, 1995). Two separate but linked two-compartment first-order pharmacokinetic models, one for the intact immunoconjugate and one for free antibody data were fit simultaneously to the intact immunoconjugate and free antibody data within the same animal. Maximum likelihood estimation, as implemented in ADAPT-II Software, was used to determine the pharmacokinetic parameters. These analyses demonstrated that the immunoconjugate of the present invention exhibits surprising in vivo stability, as measured by longer serum half-life and greater systemic exposure (i.e, area under concentration-time curve). Whereas a 1 mg dose of G17-2(anti-CD4)-PAP generated a systemic intact immunoconjugate exposure level of 3.8 $\mu$g×hour/L in 4 kg rabbits, TXU-5/B53(anti-CD4)-PAP of the present invention administered at the same dose of 1 mg/rabbit generated a 17.8-fold higher systemic intact immunoconjugate exposure level of 67.5 $\mu$g×hour/L. FIG. 2.

EXAMPLE 4

In Vivo anti-HIV-1 activity of TXU-5/B53-PAP Immunoconjugate

Mutant C.B 17 mice are used as model systems to examine the in vivo homing, engraftment, and growth patterns of normal and malignant human hematopoictic cells. Lapidot et al., Blood, 80, 32a (1992). Severe combined immunodeficient (SCID) mice, reconstituted with human peripheral blood leukocytes (hu-PBL-SCID mice), have inducible human immune function and have been shown to be useful as a surrogate model for AIDS. Mosier et al., Science, 251, 791 (1991). Hu-PBL-SCID mice could be infected with multiple strains of HIV-1 and infected mice contained virus that was recoverable by culture from the peritoneal cavity, spleen, peripheral blood, and lymph nodes for up to 16 weeks after infection. Mosier et al., cited supra. Hu-PBL-SCID mice were generated as described previously. Mosier et al., cited supra. Non-toxic doses of TXU-5/B53-PAP (20%–50% of $LD_{10}$) were administered intraperitoneally by injecting half of the total dose as a bolus and delivering the remainder i.p. over 2 weeks using Alzet micro-osmotic pumps. ZDV was added to the water at 1 mg/mL final concentration (this results in an average consumption of 200 mg/kg/day of ZDV).

Two weeks after infection with HIV-1, mice were electively killed and fresh peritoneal lavage cells as well as spleen cells were isolated, cocultured with phytohemagglutinin(PHA)-stimulated human peripheral blood mononuclear cells from an HIV-1 antibody negative donor, and culture supernatants were tested every 3–4 days for a maximum of 28 days for the presence of HIV-1 antigen with a commercially available enzyme immunoassay (Abbott Laboratories, North Chicago, Ill.) that detects primarily the core p24 antigen of HIV-1, as previously described. Goudsmit et al., J. Infectious Diseases, 155, 558 (1987). In addition to this culture method, DNA was also isolated from the peritoneal lavage cells as well as splenocytes for detection of HIV-1 DNA by PCR amplification of a 115 b.p. sequence in the gag region of the HIV-1 genome using two 29-base oligonucleotide primers, SK38 and SK39, that flank the region to be amplified. Ou C-Y et al., Science, 239, 295 (1988) DNA samples were also examined for the presence of human DNA by PCR amplification of a 110-bp fragment from the first exon of the human β-globin gene using two 20-base oligonucleotide primers, PCO3 and PCO4, that flank the region to be amplified, as previously described by Uckun et al. in *Blood*, 79, 2201 (1992).

Figure 3A:
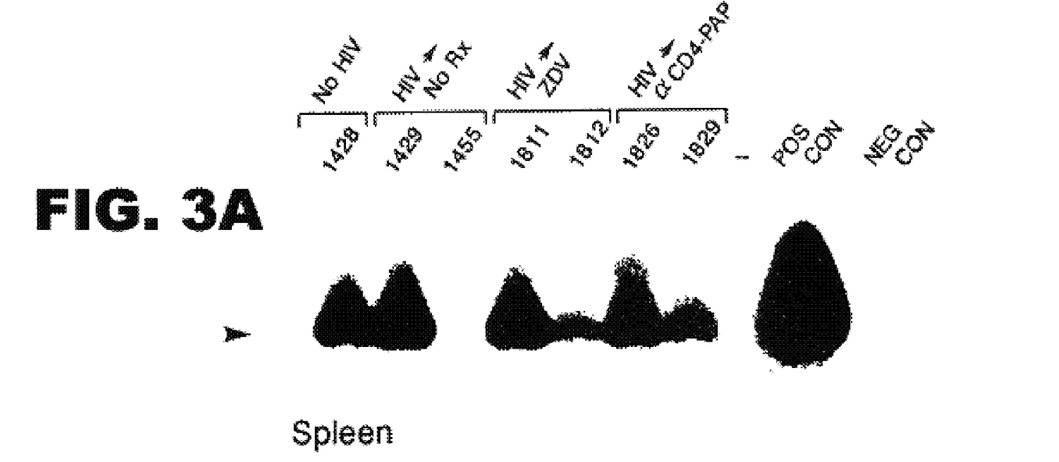
Figure 3B:
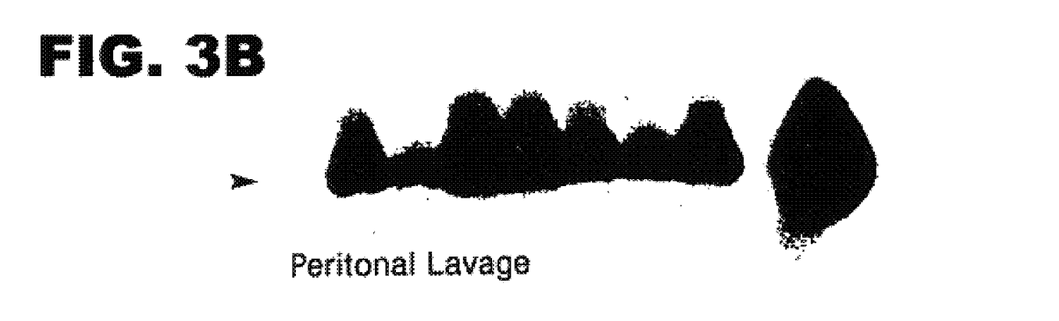
Figure 4A:
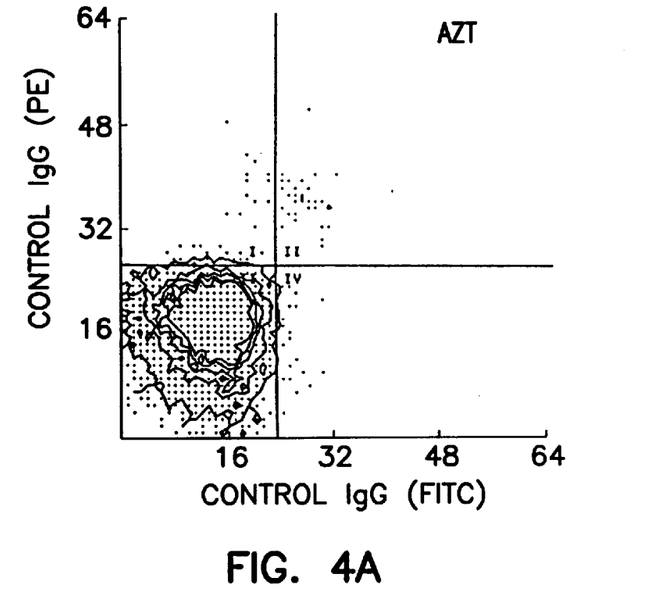
Figure 4B:
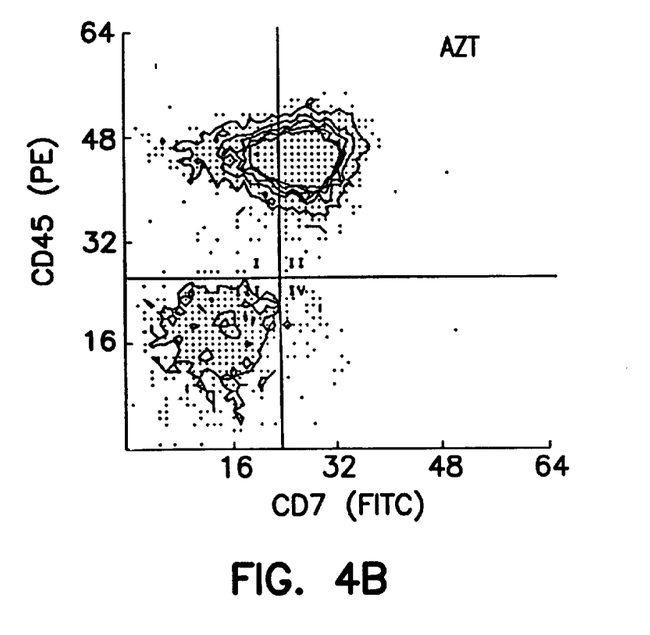
Figure 4C:
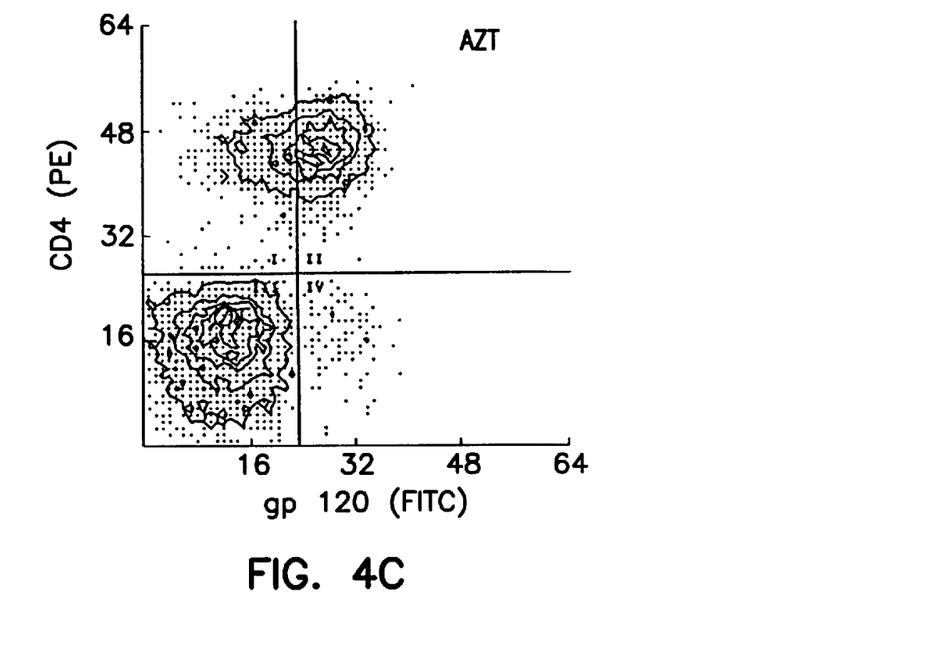
Figure 4D:
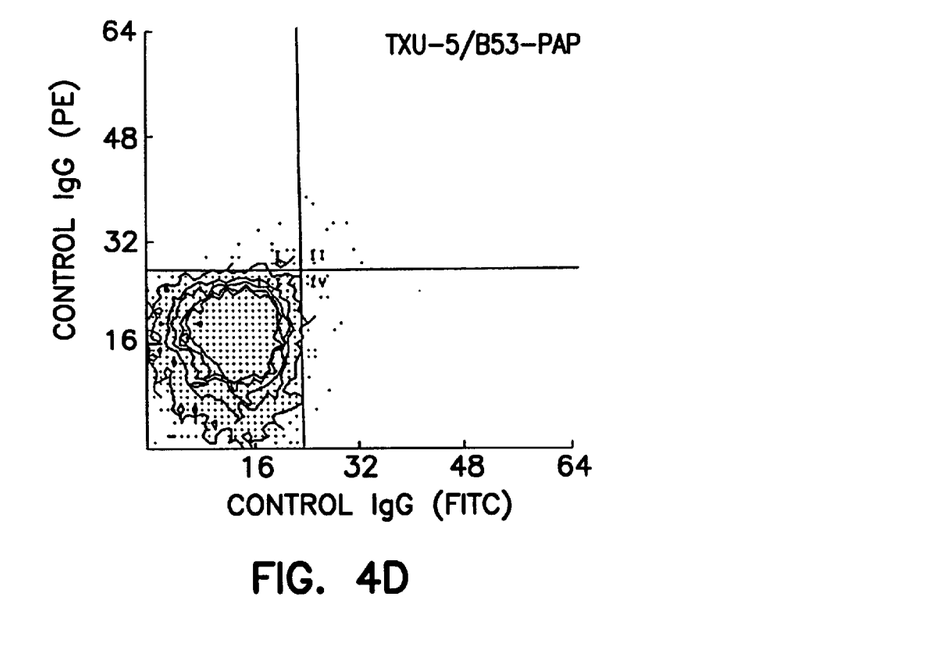
Figure 4E:
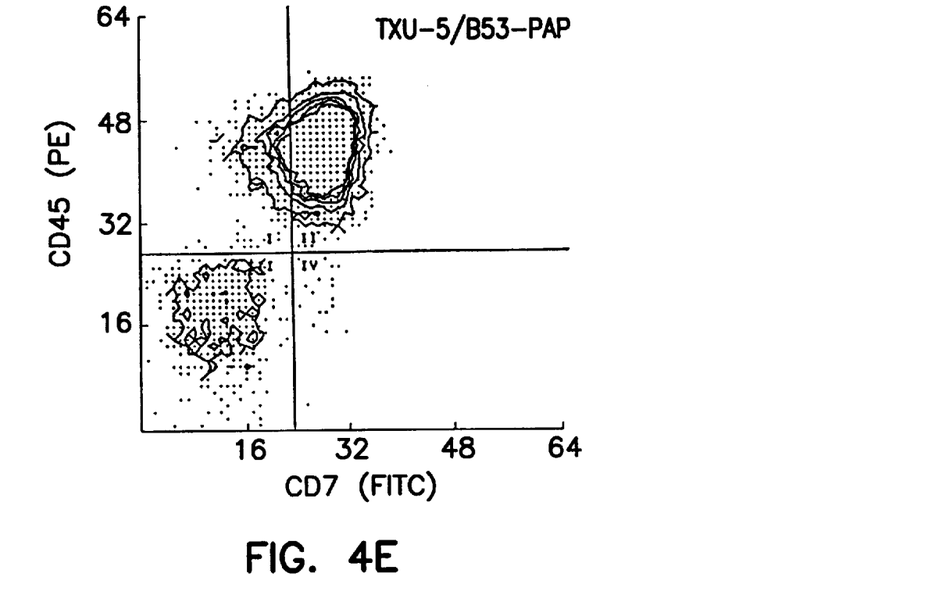
Figure 4F:
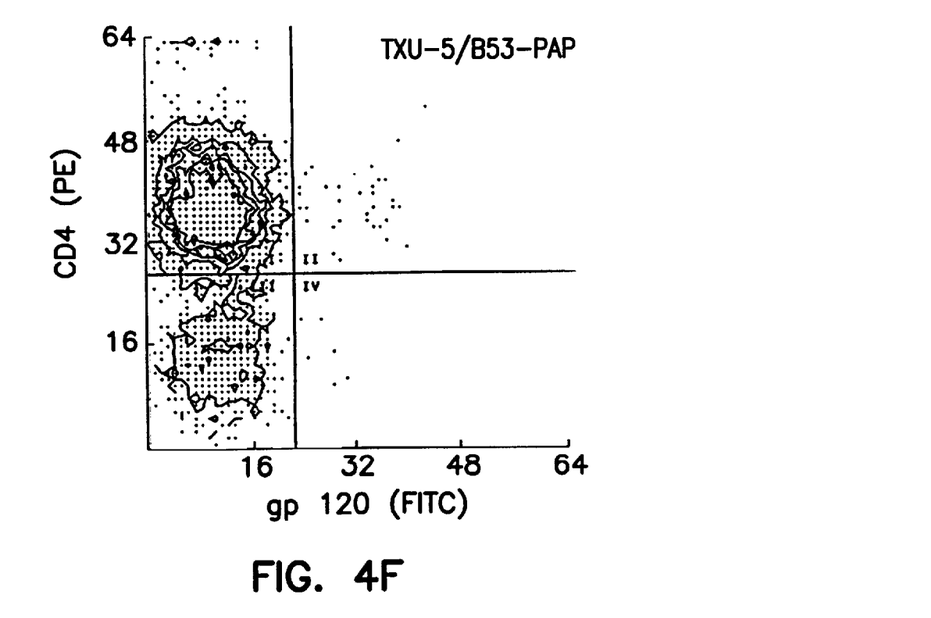
Figure 5A:
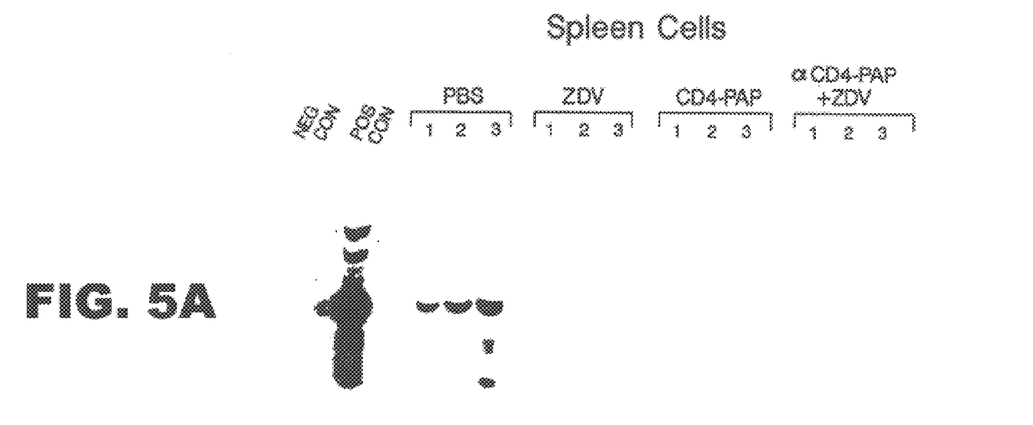
Figure 5B:
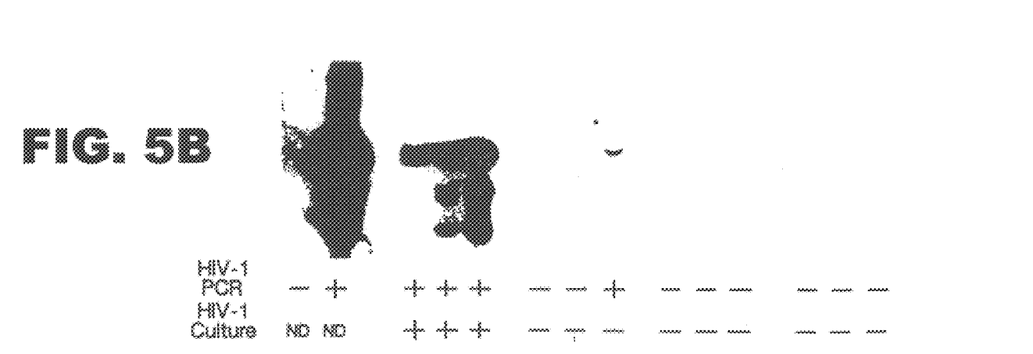
Figure 6A:
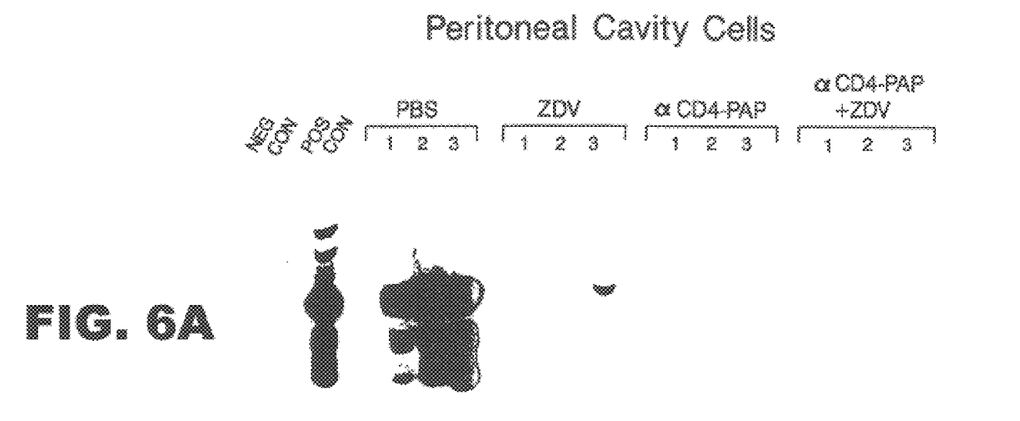
Figure 6B:
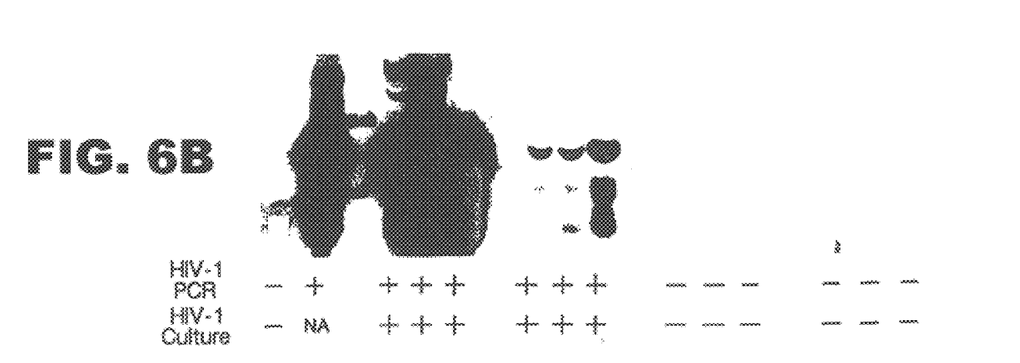

As shown in Table 1, below, of the 23 Hu-PBL-SCID mice infected with HIV-1, and treated with PBS (a) 11 were analyzed by both HIV-culture and HIV-PCR and 10 were positive in both assays while one was only positive by PCR, (b) 6 were analyzed by HIV-culture only and all 6 were positive, (c) 6 were analyzed by HIV-PCR only and all 6 were positive. By contrast, no false positive results by HIV-culture or HIV-PCR in any of the 17 control Hu-PBL-SCID mice that were not injected with HIV-1. Viral genomes were detected by PCR in 31 4 Hu-PBL-SCID mice treated with T XU-5/B53-PAP at a total dose of 20 μg but no virus was recovered by culture from any of these mice.

therapy, such engraftment was not always evident in HIV-1 infected Hu-PBL-SCID mice receiving no antiviral therapy (FIG. 3). Multiflow cytometric analysis of surface antigens on lymphocytes obtained from the peritoneal cavities of untreated or ZDV-treated mice showed presence of gpl120 on CD4+ cells consistent with persistent HIV-1 infection, whereas CD4+ cells from TXU-5/B53-PAP treated mice were gpl120 negative (FIG. 4). The detection of human DNA and CD4+ lymphocytes in TXU-5/B53-PAP treated SCID mice provided evidence that the absence of HIV-1 in TXU-5/B53-PAP treated Hu-PBL-SCID mice as not caused by absence of human CD4+ T cells due to poor engraftment or TXU-5/B53-PAP cytotoxicity to CD4+ T cells. These results are clearly superior to those obtained with ZDV alone and indicate that TXU-5/B53-PAP and ZDV can be safely combined. FIG. 5 and FIG. 6 depict the HIV-1 PCR and culture results from representative Hu-PBL-SCID mice

TABLE 1

Anti-HIV Activity of TXU-5-PAP in Hu-PBL-SCID Mice

| | | No. Infection or Treatment | PBS | HIV-1 Infection + Treatment | | | | TXU-5-PAP +ZDV |
|---|---|---|---|---|---|---|---|---|
| | | | | TXU-5-PAP | | | | |
| | | | | 20 μg | 40 μg | 60 μg | ZDV | |
| A. Cumulative Data According to Cells Analyzed | | | | | | | | |
| Peritoneal Lavage Cells | PCR+ | 0/8 | | 15/16 | 3/4 | 3/18 | 0/3 | 7/10 | 0/5 |
| | $C_x$+ | 0/4 | | 8/8 | ND | ND | ND | ND | ND |
| Spleen Cells | PCR+ | 0/8 | | 13/14 | 3/4 | 2/18 | 0/3 | 5/10 | 3/8 |
| | $C_x$+ | 0/4 | | 7/9 | ND | ND | ND | ND | ND |
| Peritoneal Lavage and Spleen Mixed | $C_x$+ | 0/12 | | 7/11 | 0/4 | 0/11 | 0/5 | 4/8/ 0/8 | |
| B. Cumulative Data According to HIV-1 Assay Used | | | | | | | | |
| PCR Only | | 1/1PCR− | | 6/6PCR+ | 1/1PCR− | 6/7PCR− | ND | 2/2PCR− | ND |
| $C_x$ Only | | 8/8$C_x$− | | 6/6$C_x$+ | ND | ND | 2/2$C_x$− | ND | ND |
| PCR + $C_x$ | | 8/8a | | 10/11c | 3/3b | 2/11b | 3/3a | 4/8c | 5/8a |
| | | | | 1/11b | | 9/11a | | 4/8b | 5/8b |
| Total No. of Hu-PBL-SCID | | 17 | | 23 | 4 | 18 | 5 | 10 | 8 |

Mice =
a PCR−$C_x$−
b PCR +$C_x$−
c PCR +$C_x$+

Notably, HIV-1 DNA was detected in only 3 of 18 Hu-PBL-SCID mice treated with TXU-5/B5 3-PAP at a total dose of 40 μg and none of the 11 mixed peritoneal lavage + splenocyte cultures from these mice were positive (Table 1). Similarly, no culture or PCR evidence of HIV-1 infection was found in any of the 5 Hu-PBL-SCID mice treated with 60 μg TXU-5/B53-PAP. In contrast to TXU-5/B53-PAP treated mice, only 3 of 10 Hu-PBL-SCID mice treated with ZDV were HIV-1 negative. Of the remaining 7 mice, 4 were culture-positive and PCR positive, and 3 cases were culture-negative but PCR-positive. Notably, of the 8 Hu-PBL-SCID mice treated with a combination of TXU-5/B53-PAP and ZDV, none were culture-positive, none (of 5 analyzed) were PCR-positive in the peritoneal cavity-derived cells, and only 3 (of 8 analyzed) were PCR-positive in the spleen.

Human DNA was detected in spleen as well as peritoneal lavage specimens from uninfected SCID mice, as well as SCID mice infected with HIV-1 but treated with ZDV or TXU-5/B53-PAP immunoconjugate, consistent with the presence of xenografted human lymphocytes. Because of the cytopathic effects of HIV-1 in the absence of appropriate challenged with HIV-1 and treated with PBS, ZDV, TXU-5/B53-PAP, or a combination of TXU-5/B53-PAP plus ZDV.

All patents and publications are incorporated by reference herein, as though individually incorporated by reference. While only certain preferred embodiments of this invention have been shown and described by way of illustration, many modifications will occur to those skilled in the art and it is, therefore, desired that it be understood that this is intended herein to cover all such modifications that fall within the spirit and scope of this invention.

What is claimed is:

1. An immunoconjugate comprising a monoclonal antibody TXU-5/B53 linked to pokeweed antiviral protein (PAP).

2. The immunoconjugate of claim 1 wherein the TXU-5/B53 antibody is produced by hybrid cell line ATCC designation HB-12261.

3. A therapeutic method comprising administering to a patient who is afflicted with HIV infection an amount of an immunoconjugate effective to reduce the viral load of said patient, wherein said immunoconjugate comprises pokeweed antiviral protein (PAP) linked to a monoclonal antibody TXU-5/B53.

4. The method of claim 3 wherein the monoclonal antibody TXU-5/B53 is produced by hybrid cell line ATCC designation HB-12261.

5. The method of claim 3 where in the immunoconjugate is administered parenterally.

6. The method of claim 5 wherein the immunoconjugate is administered in combination with a pharmaceutically acceptable liquid carrier.

7. The method of claim 6 wherein the liquid carrier comprises isotonic saline.

8. The method of claim 5 wherein the immunoconjugate is administered intravenously.

9. The method of claim 3 wherein the amount administered is about 1 mg/kg to 3 mg/kg/course.

10. The method of claim 3 wherein the administration of the immunoconjugate is accompanied by parenteral administration of an effective amount of an anti-HIV nucleoside analog.

11. The method of claim 10 wherein the anti-HIV nucleoside analog is a reverse transcriptase inhibitor.

12. The method of claim 11 wherein the anti-HIV nucleoside analog is zidovudine.

13. The method of claim 3 wherein the patient is infected with a zidovudine resistant strain of HIV.

* * * * *